US006183729B1

(12) United States Patent
Noordam et al.

(10) Patent No.: US 6,183,729 B1
(45) Date of Patent: Feb. 6, 2001

(54) STABLE VITAMIN C CONCENTRATES

(75) Inventors: Bertus Noordam, s-Gravenzande; Luppo Edens, Rotterdam, both of (NL)

(73) Assignee: Cosmoferm B.V., Delft (NL)

(*) Notice: Under 35 U.S.C. 154(b), the term of this patent shall be extended for 0 days.

(21) Appl. No.: 09/202,225

(22) PCT Filed: May 4, 1998

(86) PCT No.: PCT/EP98/02793

§ 371 Date: Dec. 10, 1998

§ 102(e) Date: Dec. 10, 1998

(87) PCT Pub. No.: WO98/50012

PCT Pub. Date: Nov. 12, 1998

(30) Foreign Application Priority Data

May 2, 1997 (NL) .................................................. 97201305

(51) Int. Cl.⁷ .......................... A61K 7/135; A61K 7/04; A61K 9/00; A61K 6/00; A61K 7/00
(52) U.S. Cl. .......................... 424/62; 424/400; 424/401; 424/59; 424/61; 514/244
(58) Field of Search .................. 424/400, 401, 424/59, 62, 61; 514/844

(56) References Cited

U.S. PATENT DOCUMENTS

| | | | |
|---|---|---|---|
| 4,940,090 | * | 7/1990 | Hoskin et al. ................. 166/270 |
| 5,455,035 | * | 10/1995 | Guerrero et al. ................ 424/401 |
| 5,728,372 | * | 3/1998 | Pinzon .......................... 424/59 |
| 5,935,584 | * | 8/1999 | Guerrero et al. ................ 424/401 |

FOREIGN PATENT DOCUMENTS

| | | |
|---|---|---|
| 0 755 674 | 7/1996 | (EP) . |
| 0 729 746 | 9/1996 | (EP) . |
| 5-1199 | 1/1993 | (JP) . |
| 5-78229 | 3/1993 | (JP) . |
| 5-078229 * | 3/1993 | (JP) . |
| 5-345714 * | 12/1993 | (JP) . |
| 7-39748 | 2/1995 | (JP) . |
| 7-223946 | 8/1995 | (JP) . |
| 94/09756 | 5/1994 | (WO) . |

OTHER PUBLICATIONS

Windholz et al The Merck Index 10th edition p. 844, 1983.*
Patent Abstract No. 66–13853F.
Patent Abstract No. 95–117984.
Patent Abstract No. 93–140292.
Chemical Abstracts No. 119:28823, vol. 119(4), pp. 16–17 (Jul. 26, 1993).
Chemical Abstracts No. 123:284274, vol. 123(21), p. 1049 (Nov. 20, 1995).
Copy of International Search Report dated Sep. 25, 1998.

* cited by examiner

*Primary Examiner*—James M. Spear
*Assistant Examiner*—Todd D Ware
(74) *Attorney, Agent, or Firm*—Morrison & Foerster LLP

(57) ABSTRACT

The present invention discloses stable vitamin C concentrates suitable for use in a multichamber dispenser. The compositions have a pH above about 5 and preferably should contain a xanthan and/or a carbomer as a viscosifier.

18 Claims, No Drawings he present invention relates to the field of topical application of vitamin C, in particular via the use of a multicompartment dispensing system.

STABLE VITAMIN C CONCENTRATES

FIELD OF THE INVENTION

The present invention relates to the field of topical application of vitamin C, in particular via the use of a multicompartment dispensing system.

BACKGROUND OF THE INVENTION

Vitamin C (ascorbic acid) has proven to possess beneficial properties when applied in cosmetic products for skin care. For instance, vitamin C stimulates collagen synthesis in the skin, thereby producing a reduction of wrinkles, it has a skin-whitening effect by interfering in the formation of melanin and it can retard skin damage caused by exposure of the skin to UV light.

Since most cosmetic products are water-based, the main focus has been on the development of aqueous formulations of this vitamin. However, the poor stability of vitamin C in aqueous formulations has been identified as a major problem in this regard.

Attempts to stabilize vitamin C are well documented. Most efforts to stabilize vitamin C compositions have been directed to minimize or prevent aerobic degradation. This can be done by adding suitable stabilizing agents, such as anti-oxidants (to prevent oxidation) and/or chelators (to complex metal ions catalyzing oxidation) (Hajratwala (1985), Rev. Sc. Pharm. of March 15). Furthermore, the pH of a vitamin C composition is found to play a role: a pH below about 3.5 has been shown to improve vitamin C stability (WO 90/12572). Additionally water activities below 0.85 have been found to stabilize vitamin C (EP 755 674).

The detrimental influence of oxygen may be circumvented by applying substantially oxygen-free conditions for preparation and storage of vitamin C compositions. Although degradation of vitamin C under anaerobic conditions is much less investigated, it has been described that this type of degradation may result in the formation of furfural and carbon dioxide (Counsel and Hornig (1981), In: Vitamin C, pp 123–137, Applied Science Publishers). Fructose and fructose derivatives appeared to stimulate this furfural/carbon dioxide production under said conditions (ibid.).

During the development by the Applicant of concentrated vitamin C compositions suitable for use in a multichamber dispensing system and for packing under substantially oxygen-free conditions, it was found that extensive gas formation occurred during preparation as well as storage of vitamin C compositions.

Of course, gas production in a closed container is an undesirable situation. Gas formation is especially unwanted in those cases that vitamin C compositions are packed in airtight containers to minimize oxidative deterioration. For instance, gas formation then will result in pressure in the compartment containing the vitamin C concentrate. In the case that a vitamin C concentrate is packed in a cartridge connected to an airless pump dispensing system, gas formation may result in inaccurate dosing of the vitamin C concentrate. More importantly, if relatively large amount of gas are formed, the plunger will be pushed out of the cartridge and the vitamin C concentrate will be released in the outer compartment of the dispenser or in the environment.

In very concentrated vitamin C formulations, the aqueous phase will be saturated with dissolved vitamin C and additionally contain a significant portion of vitamin C crystals. To guarantee an even dosage from a multicompartment dispenser, it is essential that these crystals are homogeneously suspended in the aqueous phase. Therefore a stable vitamin C concentrate should not produce any gas and at the same time any vitamin C crystals present should not precipitate.

The present invention provides several solutions to accomplish this. Furthermore, the present invention advantageously uses the anaerobic condition of the stable vitamin C concentrate to protect other active ingredients prone to oxidation against detrimental effects of oxygen.

SUMMARY OF THE INVENTION

The present invention discloses an aqueous vitamin C concentrate suitable for storage under anaerobic conditions, having a pH of at least about 5, preferably at least 6, and comprising vitamin C, optionally other oxygen-sensitive compounds and a viscosifying agent. Preferably, the viscosifying agent is selected from the group of acrylic and methacrylic polymers (Carbomers) and xanthans. The vitamin C concentration in the concentrate of the invention may range from 5 to 70%, preferably from 10 to 60%, more preferably from 20 to 60%.

The present invention further disloses a multicompartment dispensing system separately comprising a first and a second aqueous composition, said first composition being a composition having a pH of at least about 5 and comprising vitamin C and a viscosifying agent, said first and second composition generating a final composition when mixed upon dispensing, and said final composition being effective to apply vitamin C in a diluted form.

DETAILED DESCRIPTION OF THE INVENTION

The present invention discloses vitamin C compositions, in particular compositions containing high concentrations of vitamin C, which can be stored under anaerobic conditions for a prolonged time period with a minimum or low amount of gas formation.

It is shown by the present invention that gas formation occurred during preparation of a vitamin C concentrate at a relatively elevated temperature, as well as during its storage at an ambient temperature. Said phenomenon of gas formation especially was observed with compositions containing a relatively high concentration of vitamin C and a relatively low pH, in combination with certain viscosifiers.

In order to minimize gas formation during preparation and/or storage of a vitamin C concentrate, the present invention discloses that the pH of the vitamin C concentrate should not be too low, i.e. should not be less than about 5. Preferably, the pH of the vitamin C concentrates should be between 6 and 8.

The present invention further discloses that to minimize gas formation during the preparation of the vitamin C concentrate of the invention, said concentrate should not be exposed to an elevated temperature. In other words, the process for the preparation of the vitamin C concentrate should be carried out at a moderate temperature, preferably a temperature which does not exceed 50° C., more preferably a temperature which does not exceed 40° C. In particular, elevated temperatures should be avoided to minimize the degradation or oxidation of vitamin C or any of the optionally incorporated other active ingredients.

The present invention discloses a vitamin C concentrate having a vitamin C concentration which can be as high as about 70% by weight of the total composition. Preferably, the vitamin C concentration in the concentrate ranges from 5 to 70%, more preferably from 10 to 60%, most preferably from 20 to 60%. The vitamin C concentrates of the present invention are particularly suitable for use in a multichamber dispensing system.

Depending on certain characteristics of the vitamin C concentrate, such as the pH, the type of chelator and/or viscosifying agent used, and/or the vitamin C concentration, conditions may arise in which (part of the) vitamin C precipitates in the composition. As a consequence, the vitamin C concentrate is in the form of a suspension. The (partly) crystalline character of the vitamin C is an advantage rather than a disadvantage, since crystals typically display an enhanced stability.

Therefore, according to the invention the vitamin C concentrate additionally comprises a viscosifying agent which does not only minimize the formation of gas, either initially, during the process to prepare the vitamin C concentrate, as well as during storage of the concentrate, but which also is able to prevent sedimentation of particulate matter like vitamin C crystals. In other words, to stabilize a vitamin C suspension, a viscosifying agent which is a suspending agent providing a three-dimensional network is advantageously used, especially in case large crystals are present.

The viscosifying agent to be used in the vitamin C concentrate of the invention is preferably selected from the group of xanthans and acrylic and methacrylic polymers (Carbomers), such as Carbopol Ultrez 10, Carbopol ETD 2020, Carbopol ETD 2050. More preferably, said viscosifying agent is a xanthan and most preferably a brine tolerant xanthan, such as Keltrol BT.

Because of the presence of a network-forming suspending agent, the vitamin C crystals remain stably suspended in the composition.

The concentration in which the viscosifying agent is applied in the composition of the invention will depend on the type of viscosifying agent used. Typically, the concentration may vary from about 0.1 to about 5%.

Carbomer viscosifiers, which are rather salt sensitive, preferably are used in a relatively high concentration, e.g. about 2 to about 5%. Brine tolerant xanthan provides adequate viscosity at a concentration of approximately 0.2–0.3%.

The vitamin C concentrate of the invention additionally may contain one or more of an antioxidant and/or chelating agent to protect vitamin C against the harmful effects of oxygen during the process of the preparation of the composition.

After its preparation, the vitamin C concentrate of the invention may be stored in an airtight container, to prevent the occurrence of aerobic degradation. An anaerobic condition may be guaranteed by filling the container under an inert gas (such as nitrogen) blanket, or by storage under vacuum, or by total immersion of the vitamin C containing container in another liquid. In the latter situation the penetration of oxygen through the wall of the vitamin C containing container is minimal.

The vitamin C concentrates of the present invention are particularly suitable for use in a multicompartment dispensing system. Said multicompartment dispensing system comprises a first composition, which is a vitamin C concentrate according to the invention, in one compartment and a suitable second composition in a separate compartment. Upon delivery, said first and second composition are mixed, either in situ or in the dispensing system. Mixing of both compositions results in a final composition which contains vitamin C in a diluted form and which additionally is suitable for direct application, e.g. for topical use.

The nature of the. second composition will depend on the desired characteristics of the final composition, i.e. on the application which is desired. Thus, the second composition should enable, when combined with the first composition, i.e. the vitamin C concentrate, the production of a final composition which is suitable for direct application of vitamin C.

The present invention also envisages the presence of a second active ingredient in the vitamin C concentrate.

Depending on the characteristics of said second active ingredient, said ingredient may be formulated in the vitamin C concentrate by dissolution into the aqueous phase, by preparing a suspension of non-dissolved matter in the vitamin C concentrate or by preparing an emulsion in the case of a hydrophobic compound.

Examples of second active ingredients which are formulated in the first composition i.e. in the vitamin C concentrate, are active ingredients prone to oxidation. Due to the presence of a high concentration of vitamin C, the first composition is essentially free of oxygen. Typical examples of materials sensitive to oxygen include oil-soluble compounds like α-tocopherol C (vitamin E), retinol (vitamin A), polyunsaturated fatty acids (linoleic, γ-linolenic or arachidonic acid) or triglycerides incorporating high levels of such fatty acids like evening primrose oil, borage seed oil, safflower oil, sunflower seed oil or certain microbially produced oils.

To incorporate these materials homogenously into a highly concentrated solution of vitamin C, a stable oil-in-water emulsion has to be prepared using suitable emulsifiers, in combination with a xanthan or Carbomer-type viscosifyer. Emulsifiers such as certain polyglyceryl fatty acid esters are extremely useful for this purpose. Care should be taken to prepare the emulsions at a moderate temperature, e.g. 25 to 50° C. The presence of a viscosifying agent in the vitamin C concentrate according to the invention further advantageously stabilizes the emulsion in that it prevents the occurrence of phase separation.

Apart from the above-mentioned oil-soluble compounds, the stable vitamin C solution can also be used to protect water-soluble oxidation-sensitive compounds, like glutathione or thiotaurin.

The dispensing system to be used for delivery of vitamin C is not critical. Any system can be used which allows for the separate containment of the vitamin C concentrate and the second composition.

Use of a multicompartment dispensing system further provides the option to pack the vitamin C concentrate in a compartment made from non-translucent material with very low oxygen permeation rates even under conditions of high humidity, to minimize the effect of light and ingress of oxygen. Preferred packaging materials include PVdC, EVOH and alumina-coated polymers (see Food Manufacture, June 1991, pp 49–53).

However, the use of such barrier plastics to minimize the oxidation of vitamin C and thus any additional oxygen sensitive compound is not essential. Vitamin C concentrates according to the invention when incorporated in a compartment made of non-barrier plastics such as polyethylene, polypropylene, polyvinyl chloride, and the like, are surprisingly stable. Total immersion of the vitamin C containing compartment in the second composition provides so good a protection that discolourations of the vitamin C concentrate can be prevented.

If applied in larger volume dispensers, the use of an air-free lotion pump to dispense the biologically effective compound is advantageous.

A preferred multicompartment dispensing system is a dispenser containing two differently-sized compartments. Such a dispenser enables the dispensing of unequal amounts of two different compositions. Preferably, the vitamin C concentrate of the invention is placed in the smaller and a suitable second composition in the larger compartment of said dispenser.

A preferred single-use multicompartment dispensing system is a flexible package in which the heat seal separating the two chambers can be broken by applying pressure on one of the two chambers. Just before use, the seal is broken and the compositions present in the two chambers are mixed. For application, the package has to be opened e.g. by tearing, and emptied by squeezing.

Depending on the desired application, the desired vitamin C concentration in the final composition may range from about 0.1% to about 15%. The vitamin C concentration of a vitamin C concentrate for use in a multichamber dispenser thus depends on both the concentration of vitamin C which is desired in the final composition as well as the ratio in which the vitamin C concentrate and the suitable second composition are dispensed. For instance, when the desired concentration of vitamin C in the final composition is 5% and the dispensing ratio is 1 part vitamin C concentrate to 10 parts cosmetic composition, the vitamin C concentration in the first composition according to the invention is 50%.

The ratio between the vitamin C concentrate and the second composition may vary from 1:1 to 1:50 (v/v), more preferably from 1:2 to 1:20, most preferably the ratio is 1:4 to 1:10.

A crystalline form of (part of) the vitamin C can be advantageously applied in a multichamber dispensing system, since the crystals rapidly solubilize in the final composition which results after mixing of the vitamin C concentrate with a suitable second composition, especially when the vitamin C concentrate is diluted more than once in the second composition.

The multichamber dispensing system comprising a vitamin C concentrate according to the invention is especially suitable for topical application of vitamin C in pharmaceutical and/or cosmetic areas, for instance in the areas of skin whitening, UV protection and/or skin improvement, e.g. antiwrinkle.

EXAMPLE 1

Gas Production in Different Vitamin C Compositions

Vitamin C compositions (50% w/w) containing different viscosifiers (0.6% hydroxyethylcellulose (Natrosol, Hercules), 2.2% Carbopol Ultrez 10 (BF Goodrich) or 0.4% Magnafloc LT26 (Allied Colloids)) and chelators (0.2% Dequest 2010 (Boucquillon, Belgium) or 2 mM EDTA) have been prepared. All compositions contained 5 mM bisulfite final concentration. The compositions were prepared by stirring all components in the water phase for about one hour at a temperature of 65° C. to dissolve the viscosifyers.

During preparation of samples 3, 5, 6, 10 and 13 a precipitate was formed.

Small containers were filled under vacuum with sample material and closed with a plug. The samples were stored at either room temperature (RT) or 40° C. Samples were visually inspected for gas production. The results are presented in Table 1.

The gas production results clearly indicate that the viscosifier type as well as the pH have a dramatic effect on gas production. Excessive, undesirable gas production during sample preparation was observed when Natrosol was applied as viscosifier. Almost no to no gas production during sample preparation was observed when Carbopol Ultrez 10 was used. Samples containing Carbopol also gave the best results, i.e. the lowest gas production, during storage. It also became clear from all experiments that the gas production decreased with increasing pH.

On the basis of these experiments one can conclude that Carbopol is a suitable viscosifyer to minimize gas production and thus vitamin C degradation. For optimal results such a Carbopol containing composition should have a pH value of 6.0 minimal. Furthermore it would be advantageous if the composition could be prepared without a significant heating.

TABLE 1

Gas production

| Sample | pH | Viscosifier | Chelator | during sample prepn. | during storage at RT | during storage at 40° C. |
|---|---|---|---|---|---|---|
| 1 | 5.0 | Natrosol | EDTA | ++++ | + | ++++ |
| 2 | 5.0 | Natrosol | Dequest | ++++ | +/− | ++++ |
| 3 | 5.5 | Natrosol | Dequest | ++++ | 0 | +++ |
| 4 | 5.5 | Natrosol | EDTA | ++++ | +/− | ++ |
| 5 | 6.0 | Natrosol | EDTA | ++++ | 0 | + |
| 6 | 7.0 | Natrosol | EDTA | ++++ | 0 | +/− |
| 7 | 5.0 | Carbopol | EDTA | +/− | 0 | +++ |
| 8 | 5.5 | Carbopol | EDTA | +/− | 0 | ++ |
| 9 | 6.0 | Carbopol | EDTA | +/− | 0 | + |
| 10 | 7.0 | Carbopol | EDTA | +/− | 0 | 0 |
| 11 | 5.0 | Magnafloc | EDTA | + | +/− | ++++ |
| 12 | 5.5 | Magnafloc | EDTA | + | +/− | +++ |
| 13 | 6.0 | Magnafloc | EDTA | + | 0 | +++ |

0 -> ++++ from no to high gas production

EXAMPLE 2

Origin and Nature of the Gas Production

Three solutions were made:
1. 40% vitamin C, pH 3.6.
2. 40% vitamin C including 0.4% hydroxyethylcellulose, pH 3.6.
3. 0.4% hydroxyethylcellulose, pH 3.6.

The solutions were stored at 40° C. in containers closed with a plunger which could move in case gas production occurred during storage. The samples were inspected visually and in case gas production had occurred, the gas was analysed by gas chromatography.

The result was that solutions 1 and 2 demonstrated gas production and the third did not. Gas chromatographic analysis demonstrated that the produced gas was carbon dioxide ($CO_2$). It can thus be concluded that at least part of the vitamin C is subject to decarboxylation under the applied storage conditions.

EXAMPLE 3

Stability of Vitamin C Suspensions with Selected Viscosifyers

From the data reported in Example 1 it can be inferred that:

Natrosol and, to a lesser extent, Magnafloc stimulate gas production and thus decay of vitamin C;

at neutral or even alkaline pH values gas production will be minimal;

heating of the samples to 65° C. to facilitate dissolution of the viscosifyer leads to gas production and thus decay of vitamin C;

concentrated vitamin C solutions tend to form suspensions of (sodium)ascorbate upon increasing the pH value of the solutions to 7.

This suggests that maximum stability of vitamin C can be obtained at neutral pH values, at high vitamin C concentrations (and thus part of the vitamin C precipitated) and in combination with a production process that involves minimal heating only.

Other viscosifyers were tested for their usefulness in concentrated vitamin C compositions, and two product categories were selected for final tests, i.e. xanthans and carbomers. For a more detailed comparison, one xanthan (brine-tolerant, Keltrol BT, Kelco) and two carbomers (Carbopol Ultrez 10 and ETD 2050 (both from BF Goodrich) were tested with the following vitamin C composition.

Sodium ascorbate (Roche), micronized to a particle size of about 5 micron by jet-milling: 56% (w/w), Glycerol pure 20% (w/w), sodium bisulphite 0.1% (w/w), EDTA 0.1% (w/w), demin. water.

To add Keltrol BT, dry product was dissolved in the ascorbate suspension by homogenization at room temperature to reach a final concentration of 0.25% (w/w).

To add Carbopol Ultrez 10 or ED 2050, 2% (w/w) stock solutions were prepared in 50% glycerol in water. These stocks were diluted and homogenized at room temperature to give a final concentration of 0.8% (w/w) Carbopol (and 20% glycerol). After addition of the viscosifyer, the pH value of the suspension was adjusted to pH 7.0 by the addition of 8N sodium hydroxide.

The Brookfield viscosities of the three suspensions (25° C., 50 rpm, spindle SC4-29) were approx. 10.000 cP for the Carbopol material and approx. 6.000 cP for the Keltrol material.

Gas Formation and Particle Sedimentation

The stabilized vitamin C concentrates were poured in glass containers, hermetically closed and stored at 40° C. in the dark.

After 1 month of storage no gas formation was observed in either one of the three preparations. A very slight sedimentation could be observed in the concentrate stabilized with Carbopol Ultrez 10 and ETD 2050. The concentrate containing Keltrol BT exhibited no sedimentation.

Vitamin C Stability

To measure the stability of the two vitamin C suspensions, both products were introduced into small (4.5 ml content) cylinders ("cartridges") made of high density polyethylene (HDPE, wall thickness 1 mm) and closed with a polyethylene plunger. After closure no residual air bubbles were present in the small cylinder. Some of these vitamin C filled cylinders were kept frozen at −20° C. and the rest was stored at 40° C. in the dark.

After 6 weeks of storage, all of the samples were analyzed for residual levels of L-ascorbic acid. The analysis was carried out using the L-ascorbic acid test of Boehringer. According to the data obtained (Table 2), the vitamin C levels after 6 weeks at 40° C. were almost identical with the vitamin C levels determined in the samples that were kept frozen. Surprisingly, this remarkable stability can be obtained with a carbohydrate-based viscosifyer like xanthan, without creating gas problems as observed for the carbohydrate-based Natrosol viscosifyer as used in Example 1.

TABLE 2

| | Levels of L-ascorbic acid in g/kg product after storage for 6 weeks at | |
|---|---|---|
| Stabilized with | −20° C. | 40° C. |
| Carbopol Ultrez 10 | sample 1: 510 | sample 1: 500 |
| | sample 2: 510 | sample 2: 500 |
| Keltrol BT | sample 1: 510 | sample 1: 500 |
| | sample 2: 510 | sample 2: 500 |
| Carbopol ETD 2050 | sample 1: 510 | sample 1: 500 |
| | sample 2: 510 | sample 2: 500 |

EXAMPLE 4

Vitamin C Stability in Polyethylene Containers

A vitamin C concentrate stabilized with Carbopol Ultrez 10 was prepared according to the method described in Example 3. The concentrate was filled without any residual air bubbles present into the semi-transparent cartridges also described in Example 3 and closed with a polyethylene plunger so that all air between the surface of the concentrate and the plunger was pushed out.

Of these freshly prepared and packed concentrates, 2 cartridges were stored at −20° C. in the dark, 2 cartridges were stored at 20° C. in the dark and 2 cartridges were stored at 40° C. in the dark, and 2 cartridges were stored at 45° C. in the dark.

The last 2 cartridges were introduced in a small beaker filled with a standard commercially available skin cream. Both cartridges were completely submerged in the cream. After introducing the cartridges, the beaker was closed with an airtight lid containing a hole of about 1 mm diameter. This set up ensures direct contact with the atmosphere but limits the evaporation of water from the cream. The beaker with the cream and the cartridges was also placed at 40° C. in the dark.

After 16 weeks of storage at the various temperatures the content of all cartridges were judged in terms of colour development and content of L-ascorbic acid. Levels of L-ascorbic acid measured with the Boehringer test shows a residual content of L-ascorbic acid in all samples better than 95% of the L-ascorbic acid levels measured in the cartridges kept frozen for 16 weeks.

Despite these minimal differences in vitamin C content, the differences in colour development of the packed concentrates were obvious (Table 3).

TABLE 3

| Sample nr. | Stored at | Level of L-ascorbic acid | Colour |
|---|---|---|---|
| 1 | 20° C. | 100% | very light yellow |
| 2 | | | |
| 1 | 20° C. | 100% | pink |

TABLE 3-continued

| Sample nr. | Stored at | Level of L-ascorbic acid | Colour |
|---|---|---|---|
| 21 | 40° C. | 100% | brownish |
| 2 | | | |
| 1 | 40° C. submerged | 100% | light yellow |
| 2 | | | |
| 1 | 45° C. | 94% | brown |
| 2 | | | |

This example demonstrates that prolonged exposure to the air results in a homogenous discoloration the vitamin C concentrate packed in the HDPE cartridges. The higher the storage temperature the stronger the discoloration. This discoloration is obviously the effect of a slow diffusion of oxygen through the plastic wall of the cartridge because glass sealed concentrations do not develop such a discoloration.

Remarkable is that a simple submersion in a cosmetic cream is adequate to minimize this diffusion phenomenon.

EXAMPLE 5

Vitamin C Stabilises Vitamin A and Vitamin E

The following experiment illustrates that the vitamin C concentrate according to the invention is an excellent carrier for other oxidation-sensitive compounds such as vitamin E and vitamin A.

A vitamin C concentrate was prepared by mixing the following ingredients: demin. water 200 grams, glycerol 188 grams, sodium ascorbate (Roche) 1 52 grams, Dequest 2010 (Monsanto) 1.3 ml, Keltrol BT (Kelco) 3.6 grams and sodiumbisulphite 0.6 grams. After complete dissolution of the various ingredients, more water was added to obtain a final weight of 600 grams.

By adding 8N sodiumhydroxide the pH value of the solution is adjusted to 7.0. Due to the relatively low concentration of sodium ascorbate, a clear solution was obtained.

As reference material, exactly the same formulation was prepared but without adding sodium ascorbate, demin. water was added instead.

As both vitamin E and vitamin A are oil soluble compounds, emulsifiers have to be added to homogeneously incorporate these vitamins into the aqueous vitamin C concentrate and the reference liquid without vitamin C.

To that end, 100 grams of vitamin E (DL-α-tocopherol, BASF) and 100 grams of vitamin A (Retinol 10 CM containing approx. 10% active ingredient, BASF) were each homogenized with 3 grams of Tween 80 (ICI) and 2 grams of sorbitan monostearate (ICI) at a temperature of 45° C. and under a blanket of nitrogen gas and using yellow light. Then 20 grams of each emulsifier-oil mixture was added to 180 grams of the aqueous vitamin C concentrate as well as the reference liquid also heated to 45° C. and thoroughly homogenized. The resulting oil-in-water emulsions were filled in either reagent tubes (closed but with considerable headspace) or in the HDPE cartridges described in Example 3 (closed and no headspace).

Reagent tubes and cartridges were incubated as such at either 22° C. or at 40° C. in the dark. After 0, 7 and 18 days of incubation, the levels of vitamin E and vitamin A were measured in the various samples. Analyses were carried by HPLC essentially as described by E. Doughty et al. (Food Beverage, Vol 15, No 5, p 4 and 5). The emulsions were removed from their containers and homogenized before taking samples.

Samples of approx. 400 mg were introduced into a 100 ml volumetric flask after which 10 ml of water was added. Subsequently 60 ml of ethanol was added and the mixture was carefully homogenized for 10 minutes. Finally ethanol was added to 100 ml followed by another homogenization. Part of the resulting liquid was centrifuged and a sample of the clear liquid was injected in HPLC equipment with a Beckman Ultrasphere ODS, 5 micron, 250×4.6 mm column. Eluens used was a methanol-water (98+2 v/v) mixture; vitamin A was detected at 325 nm and vitamin E at 290 nm wave length. Concentration at t=0 days represent averages from all samples, the other figures represent averages from all samples, the other figures represent the average value of two measurements.

The data shown in Table 4 clearly indicate the protective effects of the vitamin C concentrate in the cartridge on the degradation of both vitamin E and vitamin A.

TABLE 4

| Sample | Storage condition | Temperature ° C. | 0 | 7 | 18 |
|---|---|---|---|---|---|
| | | | Concentration vitamin E (grams/100 gram emulsion) after (days) | | |
| 1 | vit C/cartridge | 22 | 9.1 | 8.8 | 9.1 |
| 2 | reference/cartridge | 22 | 9.1 | 9.0 | 8.6 |
| 3 | reference/test tube | 22 | 9.1 | 8.9 | 9.2 |
| 4 | vit C/cartridge | 40 | 9.1 | 9.1 | 9.3 |
| 5 | reference/cartridge | 40 | 9.1 | 8.5 | 8.2 |
| 6 | reference/test tube | 40 | 9.1 | 9.5 | 8.5 |
| | | | Concentration vitamin A (grams/100 gram emulsion) after (days) | | |
| 7 | vit C/cartridge | 22 | 0.93 | 0.97 | 0.96 |
| 8 | reference/cartridge | 22 | 0.93 | 0.83 | 0.91 |
| 9 | reference/test tube | 22 | 0.93 | 0.78 | 0.69 |
| 10 | vit C/cartridge | 40 | 0.93 | 0.96 | 0.95 |
| 11 | reference/cartridge | 40 | 0.93 | 0.93 | 0.78 |
| 12 | reference/test tube | 40 | 0.93 | 0.79 | 0.60 |

EXAMPLE 6

Preparation of an Emulsion Containing Vitamin C and Another Skin Lightening Agent Linoleic acid or related polyunsaturated compounds like linoleic acid esters or triglycerides incorporating high levels of this polyunsaturated fatty acids are, like vitamin C, claimed to be effective in skin lightening (see for example J05194176). It would therefore be advantageous to combine the vitamin C concentrate according to the invention with these skin lightening unsaturated compounds. Not only because of the stabilizing effect exerted by vitamin C (see for example J.Biol.Chem. 259, 4177–4182, 1984) but also because of the synergistic skin lightening effect.

To incorporate linoleic acid into the vitamin C concentrate, a stable oil-in-water emulsion has to be prepared. To minimize any oxidation reactions, such an emulsion is preferably prepared without excessive heating. Suitable emulsifiers are preferably selected from the group of polyglyceryl fatty acid esters, such as the Decaglyn product range from Nikkol (Japan). To prepare a stable emulsion, first a solution containing 25% (w/w) of sodium ascorbate, pH 7, was prepared. This solution was mixed at room temperature with the xanthan Keltrol BT to reach a final concentration of 0.7% xanthan. Then, 5 ml of decaglyceryl monoisostearate (Decaglyn 1-IS) was mixed with 20 ml of linoleic acid (Edenor SB, Henkel, Germany) at 35° C. Finally, 80 ml of sodium ascorbate/Keltrol solution and 20 ml of the linoleic acid/emulsifier mixture were vigorously mixed for a few minutes at 35° C. This yielded a stable emulsion.

What is claimed is:

1. An aqueous vitamin C concentrate that is stable to aerobic degradation and has a pH of at least about 5, comprising vitamin C and a viscosifying agent selected from the group consisting of (i) acrylic and methacrylic polymers and (ii) xanthans.

2. The composition of claim 1, wherein the viscosifying agent is a xanthan.

3. The composition of claim 1, wherein vitamin C has a concentration of 5 to 70% (w/w).

4. The composition of claim 1 further comprising a second active ingredient.

5. The composition of claim 4, wherein the second active ingredient is vitamin E or vitamin A or a mixture thereof.

6. The composition of claim 4, wherein the second active ingredient is linoleic acid, an ester of linoleic acid, or a triglyceride incorporating linoleic acid, or an ester of linoleic acid.

7. The composition of claim 5, wherein the composition is an emulsion.

8. A multicompartment dispensing system separately containing a first and a second aqueous composition, said first composition being a composition according to claim 1, said first and second composition generating a final composition when mixed upon dispensing, and said final composition being effective to apply vitamin C in a diluted form.

9. The dispensing system of claim 8, wherein the first composition is packed under anaerobic conditions.

10. The dispensing system of claim 8, wherein the compartment containing the first composition is immersed in the second composition.

11. The composition of claim 2, wherein the xanthan is a brine tolerant xanthan.

12. The composition of claim 1, wherein vitamin C has a concentration of 10 to 60% (w/w).

13. The composition of claim 1, wherein vitamin C has a concentration of 20 to 60% (w/w).

14. A method for the preparation of the vitamin C composition of claim 1 which comprises homogenizing the vitamin C composition at a temperature which does not exceed 50° C.

15. A method for the preparation of the vitamin C composition of claim 1 which comprises homogenizing the vitamin C composition at a temperature which does not exceed 40° C.

16. A method for the topical application of vitamin C which comprises dispensing the vitamin C from the multicomponent dispensing system of claim 8.

17. The composition of claim 1, which is in an airtight package.

18. The composition of claim 1, wherein the pH is at least about 6.

* * * * *